United States Patent [19]

Lee et al.

[11] 4,452,903
[45] Jun. 5, 1984

[54] ASSAY METHOD AND REAGENT KIT MEANS FOR LIPID-CONTAINING BODY FLUID

[76] Inventors: Jin P. Lee, 1396 Trevino Dr., Troy, Mich. 48098; Ching Sui A. Yi, 28071 Everett, Southfield, Mich. 48076

[21] Appl. No.: 235,206

[22] Filed: Feb. 17, 1981

[51] Int. Cl.$^3$ .................. G01N 33/56; G01N 33/58; G01N 33/60; B65D 71/00
[52] U.S. Cl. ................... 436/540; 436/542; 436/804; 436/808; 436/826; 436/817; 422/61
[58] Field of Search .................. 424/1, 12; 23/230 B; 422/61; 436/540, 542, 804, 808, 817, 826

[56] References Cited

U.S. PATENT DOCUMENTS

| | | | |
|---|---|---|---|
| 3,816,262 | 6/1974 | Monte et al. | 23/230 B |
| 3,997,470 | 12/1976 | Monte et al. | 23/230 B |
| 4,121,975 | 10/1978 | Ullman et al. | 424/12 |
| 4,148,869 | 4/1979 | Deaton | 424/1 |
| 4,208,479 | 6/1980 | Zuk et al. | 424/8 |
| 4,235,866 | 11/1980 | Thoma | 424/1 |
| 4,235,869 | 11/1980 | Schwarzberg | 424/1 |

OTHER PUBLICATIONS

The Merck Index, 8th Edition, Merck and Co., Rahway, N.J., 1968, pp. 848–849.
Engval et al., J. Immunol., 109(1), Jul. 1972, pp. 129–135.

*Primary Examiner*—Christine M. Nucker
*Attorney, Agent, or Firm*—Krass & Young

[57] ABSTRACT

A method and reagent kit means are provided for assay of a selected hapten in an aliquot of body fluid containing lipid. The method comprises the steps of constituting the aliquot in a mixture with surfactant and incubating the mixture to solubilize the same. The content of hapten in the incubated mixture is taken up selectively by hapten-specific antibody and read by hapten non-lipid conjugate tracer assay.

18 Claims, No Drawings

ASSAY METHOD AND REAGENT KIT MEANS FOR LIPID-CONTAINING BODY FLUID

DESCRIPTION

This invention relates broadly to a new assay method and reagent kit means for determining the concentration of a selected hapten in lipid-containing body fluid.

BACKGROUND OF THE INVENTION

Various diagnostic assays for the in vitro determination of haptens in body fluid are known, including specifically: radioimmunoassay (RIA), competitive protein-binding radioassay (CPB), enzyme immunoassay (EIA), enzyme multiplied immunological technique (EMIT), enzyme linked immunosorbent assay (ELISA), fluorescent immunoassay (FIA), and hemagglutination inhibition (HAI) assay. The assays are based on the principle of optimizing the mutual affinity between the hapten (sometimes referred to herein as compound, antigen, or ligand) and a specific antibody or other binding entity for that hapten. Inherent in these assays is the need for the physical joining of molecules of the hapten and binder. However, the haptens are frequently bound to specific binding proteins or lipoproteins, for example, thyroxine to thyroid binding protein and testosterone to testosterone binding protein. This hapten binding interferes with the intended hapten-binder joining. Also, the lipids present in body fluid such as blood plasma or serum ordinarily retard this joining, for example, by physical blocking of the two reactants or by combination or binding with either reactant. Prior attempts to overcome this problem have been unduly time-consuming and expensive. Radioimmunoassay and related methodologies (competitive protein binding radioassays, etc.) have traditionally been restricted to measurement of the "free" portion of a selected hapten when the hapten exists as a protein or lipoprotein complex. Only that percentage of the total hapten concentration in any body fluid which existed free of protein or lipoprotein association was available to join with the exogenous binder employed for purposes of the assay. The only remedy prior to this invention to accomplish a total hapten measurement was to disassociate the hapten-protein bond by means of an organic extraction or other laborious procedure (ultracentrifugation, dialysis, etc.).

The incorporation of surfactant as will be described subsequently serves to break the endogenous hapten binding and make the total concentration available to join with another binding entity unaffected by the presence of surfactants. This surfactant may be combined with the exogenous binder to allow a direct assay of total hapten, completely free of extra manipulative procedures. These attempts have included, for example, ultracentrifugation, microfiltration, alkaline hydrolysis and extraction with organic solvents to remove lipids, and selective dialysis and extraction to isolate the non-lipid fraction. Despite these attempts, the art has lacked an effective method, and especially a cost-effective method, of assaying lipid-containing body fluid.

It is therefore an object of the present invention to provide cost-effective means for assaying the content of selected protein or lipoprotein bound hapten (compound, antigen or ligand), by direct assay without prior extraction or pretreatment.

A further object of the invention is to provide broadly applicable means for immunoassay of any of various exogenous or endogenous haptens, compounds, antigens or ligands in lipid-containing body fluid such as serum or plasma.

These and other objects, features and advantages of the present invention will become apparent from the following description.

SUMMARY AND DETAILED DESCRIPTION

In one aspect, the invention concerns a method for determining the concentration of a selected hapten in an aliquot of body fluid containing lipid. The method comprises constituting the aliquot in a mixture comprising surfactant, and optionally comprising lipase, and incubating the mixture to solubilize the same. The resulting incubated mixture can, in accordance with the invention, be assayed further for its hapten content by any suitable immunoassay procedure, without interference from lipids, lipoproteins, carrier proteins and the like. The term "to solubilize" as used herein in the context of the invention means to convert the selected hapten in the mixture from bound form with protein and/or lipid to free form such that the true free and bound hapten content can be directly measured by available immunoassay methods without other special pretreatment of the sample or aliquot. Lipase can be used routinely and although not essential for low lipid fluids, is preferred especially in cases where the fluid aliquot or sample is relatively high in lipid. In a preferred procedure, described below, the incubation is carried out with an antibody binding site mixture comprising surfactant and optionally lipase, together with (1) a tracer comprising a non-lipid conjugate of the hapten and (2) a first antibody which is specific to the hapten. Thus, the incubation serves simultaneously not only to free the hapten from its protein or lipoprotein bond and remove interfering lipids but also to bind the selected hapten, tracer hapten and hapten-specific antibody. The method of the invention thus avoids the need for elaborate separation procedures such as ultracentrifugation, microfiltration, extraction and dialysis. The incubation is carried out in any suitable way using surfactant or surfactant and lipase. One preferred procedure is to mix the components well and hold the mixture with warming preferably at 35°-37° C., preferably under neutral or slightly basic conditions, for about one hour, at which time the thus incubated sample is free of interfering lipids. For the incubation, one uses surfactant in sufficient concentration to solubilize the incubation mixture. One or more of a wide variety of cationic, anionic and nonionic surfactants which serve to lower surface tension can be used, the anionic and nonionic surfactants being preferred. For a comprehensive description of surfactants, see Rosen and Goldsmith, Systematic Analysis of Surface-Active Agents, 2nd Ed., Wiley-Interscience, New York, 1972. Among the preferred representative surfactants are Brij ® polyoxyethylene (4-20) lauryl ethers, polyoxyethylene (2-20) cetyl ethers, polyoxyethylene (2-20) oleyl ethers and polyoxyethylene (2-20) stearyl ethers; Tween ® polyoxyethylene sorbitan laurates, palmitates, stearates and oleates; dodecyl alcohol polyethoxyethylene ether (Thesit ®); sodium tetradecyl sulfate (tergitol 4) and sodium lauryl sulfate; dioctyl, bis(1-methylamyl), diamyl, and di-isobutyl sodium sulfosuccinate; and octylphenoxy polyethoxyethanol (Triton X) and oxyethylated tertiary octylphenol formaldehyde polymer (Triton A-20). The concentration of surfactant used in the incubation mixture is subject to wide variation and is not critical. Preferably, one uses a low concentration, e.g., not exceeding about 0.1 to 1.0% (w/v) of surfactant. Lipase (LPS; EC 3.1. 1.3) used in the incubation, preferably in purified form, is available from commercial sources; cf. Rubin, Industrial Enzymes, The Mitre Corp., 1971. Sufficient lipase is used to achieve conversion of lipid-bound hapten to unbound hapten. A concentration of about 4000 to 8000 units of lipase per cc. of patient serum or plasma is preferred.

The method of the invention is applicable for measuring any of a wide variety of haptens, compounds, antigens and ligands which are measurable by conventional immunoassay methods. Among these may be mentioned estrone, estriol, estradiol, testosterone, androsterone, androstenedione, progesterone, cortisol, aldosterone, 11-deoxycorticosterone, thyroxine (T4), triidothyronine (T3), vitamin $B_{12}$, folic acid, and the like. The method as applicable to body fluids in general and to blood plasma, serum, spinal fluid and urine in particular.

In another aspect, the invention concerns a method for assay of a selected hapten in an aliquot of body fluid containing lipid, which comprises constituting the aliquot in a mixture comprising surfactant (or surfactant and lipase), a tracer which includes a non-lipid conjugate of said hapten, and antibody which has binding sites that are specific to said hapten, and incubating the mixture to solubilize the same, and bind the unbound hapten with the hapten specific antibody. The method advantageously serves not only to solubilize the mixture and free it from potentially interfering lipids but also to bind the selected hapten with the hapten-specific antibody which at the desired endpoint can be isolated and read quantitatively for its hapten content. As described above, one uses surfactant and also a tracer which includes a specific hapten conjugate which preferably is radiolabeled or, in another different, non-radioactive but preferred embodiment, is a specific hapten enzyme conjugate that in a suitable system provides a convenient photometric hapten-content readout. The latter system, for example, may include as components: (1) the hapten enzyme conjugate such as testosterone-3-carboxymethyloxime conjugate to the enzyme malate dehydrogenase (MDH), (2) antibody which has binding sites for a desired specific hapten such as testosterone, (3) substrate for the enzyme such as malic acid or oxalacetic acid, and (4) cofactor or coenzyme such as nicotinamide dinucleotide (NAD) or its reduced form NADH, respectively. This illustrative system which is reversible involves the desired endpoint production of NAD (oxaloacetic acid substrate) or the reduced form of NAD which is NADH (malic acid substrate). The quantitative presence of NADH is a measure or function of the content of the specific hapten in the sample and is readily and reproducibly readable in the assay by photometric means. A more complete description of the system and related systems is contained in U.S. Pat. Nos. 3,817,837, 3,852,157, 4,067,774 and 4,191,613, incorporated herewith by reference. The tracer or marker employed which includes the specific hapten conjugate is conventional, and its choice per se does not form a part of the invention. For a radiolabeled tracer, the active component is a radioactive non-lipid conjugate of the hapten being assayed. A wide variety of such conjugate materials are available commercially or can be made by known procedures; cf. Tantchou et al., J. Immunoassay, 1(1), 129–47 (1980). The following are illustrative: testosterone $^{125}$I, estrial $^{125}$I, 17-beta-estradiol $^{125}$I, DHEA-sulfate $^{125}$I, progesterone $^{125}$I, and cortisol $^{125}$I. For an enzyme tracer, the active component is the enzyme conjugate of the hapten being assayed. A wide variety of such conjugate materials can be made by known procedures (cf. U.S. Pat. No. 4,191,613) of which materials the testosterone-3-carboxymethyloxime, 3-(0-carboxymethyl) estradiol and triiodothryonine conjugates to MDH are illustrative.

The antibody used in the assay is any suitable antibody having binding sites that are specific to the hapten being measured. Thus, as an example, for the assay of testosterone in an aliquot of human serum, one uses in the incubation an anti-human testosterone anti-serum prepared in vivo from another mammal species such as the rabbit.

In a preferred embodiment of the assay method of the invention, the tracer conjugate is radioactive and the incubation mixture containing the first, hapten-specific antibody is incorporated with a second antibody which is specific to the first, hapten-specific antibody. After mixing, the resulting radioactive hapten-first antibody-second antibody product is then isolated, as by centrifugation, and the radioactivity of the product is counted, from which the hapten content can be determined by reference to calibrator samples and controls. Preferred first and second antibodies for the assay are rabbit anti-human hapten anti-serum and goat anti-rabbit hapten antibody, respectively.

A preferred embodiment of the invention is a reagent kit for assay of a selected lipid-bound and unbound hapten in an aliquot of body fluid containing lipid or lipoprotein comprising a tracer including a non-lipid conjugate of the hapten, preferably radio-active; first and second competitive binding proteins for immunospecific mutual binding with the hapten and conjugate; and means for constituting surfactant or surfactant and lipase in an incubation mixture with the aliquot for solubilizing the mixture. Preferably, the tracer is in the form of an aqueous solution in a first container, preferably containing the surfactant. The first antibody is in a separate container, preferably containing a lipase. The second antibody is separately contained. In carrying out the assay, the reagents are diluted or reconstituted with water, where necessary, and constituted together as required.

In another preferred embodiment, the reagent kit, for assay of a selected hapten comprises a non-lipase enzyme conjugate with the hapten, preferably hapten malate dehydrogenase conjugate; enzyme substrate; coenzyme; antibody specific to the hapten; and means for constituting surfactant or surfactant and lipase in an incubation mixture with the aliquot for solubilizing the mixture. A preferred embodiment is one where the hapten is testosterone and the non-lipase enzyme is MDH, the coenzyme being NAD or NADH and the substrate malic acid or oxaloacetic acid, respectively.

The invention is illustrated by the following examples.

ASSAY METHOD

Materials and Reagents

A. $^{125}$I-Testosterone Tracer Solution . . . One bottle (20 cc.) of $^{125}$I-0-(2-iodohistaminyl carboxamidomethyl) testosterone oxime in aqueous solution, activity less than 4 microCuries. Contains 0.01 M phosphate buffer ph 7.5, 0.25% BBG, 0.85% EDTA, 1.0% (w/v) polyoxyethylene 9 lauryl ether, and 0.05% sodium azide as preservative.

B. Testosterone Antiserum . . . One bottle (20 cc.) containing lyophilized rabbit anti-human testosterone antiserum in 0.01 M phosphate buffer pH 7.4, 0.25% BSA, 0.1 mg/ml lipase and 0.1% Sodium Azide.

C. Testosterone Standards . . . Seven bottles (2 cc. each) containing a lyophilized solution of 0.0, 25, 50, 125, 250, 500 and 1000 ng/dl of testosterone in bovine serum base and 0.1% sodium azide as preservative. Store at 2°–8° C. Reconstitute with 2.0 cc of distilled water. Let stand 10 minutes to dissolve and mix well by gentle inversion.

D. Testosterone Controls . . . 2 bottles (2.0 cc. each) containing purified human testosterone in a lyophilized bovine serum base adjusted to normal levels of male and female hormone concentrations and 0.1% sodium azide. Reconstitute with 2.0 cc of distilled water. Let stand 10 minutes to dissolve and mix well by gentle inversion. Store at 2°–8° C.

E. PEG-2nd Antibody Solution . . . One bottle (100 cc) containing polyethylene glycol (PEG) 6% w/v and goat antirabbit antibody, 0.05% BSA and 0.1% sodium azide. Store at 2°–8° C.

F. Balance Buffer . . . One bottle (5 cc) containing a solution of Normal Saline and Bovine gamma globulin. Store at 2°–8° C.

Procedure Instructions

1. Label duplicate 12×75 mm glass or polypropylene assay tubes for each standard, control and patient.
2. Pipette 0.1 cc of each standard, female control and female patient to the appropriately labeled tubes.
3. Pipette 0.05 cc of male control and male patient to the appropriately labeled tubes.
4. Add 0.05 cc of Balance Buffer to each male control and male patient tube.
5. Add 0.2 cc of $^{125}$I-Testosterone Tracer Solution and 0.2 cc of Testosterone Antiserum Solution to all tubes.
6. Mix well and incubate at 37° C. for one hour.
7. After incubation, dispense 1.0 cc of PEG-2nd Antibody Solution to all tubes.
8. Mix well by vortexing and centrifuge at 1500×g for a minimum of 20 minutes.
9. Decant off the supernatant liquid, but do not allow the tubes to remain inverted for more than a minute before blotting the rims and placing upright.
10. Determine the radioactivity of the precipitate remaining in each tube by counting in a gamma scintillation counter for a period of time not less than that necessary to obtain 10,000 counts in the zero standard tubes.

FLOW CHART

| Sample | Serum or Plasma | Balance Buffer | $^{125}$I Testosterone Tracer | Testosterone Antiserum | | PEG-2nd Antibody | |
|---|---|---|---|---|---|---|---|
| 0, 25.0, 50.0, 125 250, 500 100 ng/ml standards | 0.1 cc | — | 0.2 cc | 0.2 cc | Mix & Incubate at 370° C. for one hour | 1.0 cc | Mix & Centrifuge for 20 min. at 1500 ×g |
| Female Control | 1.0 cc | — | 0.2 cc | 0.2 cc | | 1.0 cc | |
| Male Control | 0.05 cc | 0.05 cc | 0.2 cc | 0.2 cc | | 1.0 cc | |
| Female Patients | 0.1 cc | — | 0.2 cc | 0.2 cc | | 1.0 cc | Decant and |
| Male Patients | 1.05 cc | 0.05 cc | 0.2 cc | 0.2 cc | | 1.0 cc | count |
| Nonspecific Binding | 0.1 cc (Std) | 0.2 cc | 0.2 cc | — | | 1.0 cc | ppt. |

Specimen Collection

Sample: Serum (0.3 cc), no additives or preservatives are needed to maintain the integrity of the specimen, however, plasma collected with EDTA may be employed in lieu of serum. Grossly hemolyzed samples should not be used.

Storage: Store refrigerated (2°–8° C.) unless analysis will be delayed beyond 48 hours. Then store frozen (−20° C.). Avoid repeated freezing and thawing.

Patient Considerations: No special patient preparation is necessary except to determine the possible existence and interfering effect of radiation from previous therapy or nuclear medical diagnostic testing.

Assay Procedure

Materials

1. Semi-automatic pipettes (0.05 and 0.1 cc).
2. Precision semi-automatic dispenser (1.0 cc).
3. Vortex mixer.
4. Test tube racks.
5. Centrifuge capable of obtaining 1500×g.
6. Gamma scintillation counter.

Procedural Notes

1. All reagents including patients and control serums should be brought to room temperature and mixed thoroughly before beginning the assay.
2. Centrifugation at 1000×g may be used, but the time should be increased to 30–40 minutes.
3. Care should be taken in the decanting step. Due to the small amount of protein precipitate, any loss will greatly affect results.
4. For quantitation of patient samples exceeding 2000 ng/ml, first dilute the patient 1:1 with the zero standard. Then use 0.05 cc of diluted patient and 0.05 cc of balance buffer as in the protocol for a normal male sample.
5. Male patients regardless of age should be run with 0.05 cc of sample and 0.05 cc of balance buffer. Falsely lowered results will be obtained if 0.1 cc of sample is employed.
6. As in any classical radioimmunoassay, total count and non-specific binding (NSB) tubes may be added. The total count is obtained by pipetting 0.2 cc of Tracer to an assay tube, capping and counting at the end of the determination. NSB is found by substituting 0.2 cc of balance buffer for the antiserum as shown in the flow chart. Typically, the non-specific binding of the assay is less than 5% B/t. Bo/T must exceed 20%.

Calculation of Results

1. Determine the average cpm for each pair of duplicate tubes.
2. Derive B/Bo for each standard, control and patient as follows:

$$\% B/Bo = \frac{B - NSB}{Bo - NSB} \times 100$$

B=mean count rate for each pair of tubes.
Bo=mean count rate for the zero standard.
NSB=mean count rate for the non-specific binding tubes.

3. Construct a standard curve by plotting the %B/Bo of each standard against its concentration in ng/ml on logit-log graph paper.
4. Obtain the value of each patient and control by reference to the standard curve. Male testosterone results from the curve must be multiplied by two. Note: Any diluted samples must be further converted by the appropriate dilution factor.

SAMPLE DATA

| Tube | Sample | Average Count | Net Count | % B/Bo | ng/dl |
|---|---|---|---|---|---|
| 1,2 | 0.0 | 25396 | 23733 | 100 | |
| 3,4 | 25 | 18220 | 16557 | 69.8 | |
| 5,6 | 50 | 15311 | 13648 | 57.5 | |
| 7,8 | 125 | 11907 | 10244 | 43.2 | |
| 9,10 | 250 | 8727 | 7064 | 29.8 | |
| 11,12 | 500 | 6097 | 4434 | 18.7 | |
| 13,14 | 100 | 4148 | 2485 | 10.4 | |
| 15,16 | NSB | 1663 | — | — | |
| 17,18 | Female Control | 13952 | 12289 | 51.8 | 82 |
| 19,20 | Male Control | 7321 | 5658 | 23.8 | 360 × 2 = 720 |
| 21,22 | Female Patient | 14514 | 12871 | 54.2 | 73 |
| 23,24 | Male Patient | 10802 | 9139 | 38.5 | 158 × 2 = 316 |
| 25 | Total | 43766 | — | — | |

$NSB = \frac{1663}{43766} \times 100 = 3.8\%$ $Bo/T = \frac{25396}{43766} \times 100 = 58\%$ Example: Male Patient
Average net count of zero standard = 23733
Average net count of patient = 9139

$\% B/Bo = \frac{9139}{23733} \times 100 = 38.5\%$

By interpolation from the standard curve, it can be determined that the %B/Bo of 38.5% corresponds to a testosterone value of 158 ng/dl or a final patient hormone concentration of 316 ng/dl.

For comparison, the above assay for serum testosterone was repeated in separate runs with and without the surfactant (in this instance the surfactant was 0.4% Triton ®x-100 instead of polyoxyethylene lauryl ether). The following typical assay results illustrate the effect of the addition of the surface active agent on the performance of the assay:

| NO DETERGENT ADDED | | | 0.4% TRITON X-100 ADDED TO ANTISERA | | |
|---|---|---|---|---|---|
| Sample | Count | Value (ng/ml) | Sample | Count | Value (ng/ml) |
| 0 STD | 18980 | — | 0 STD | 10318 | — |
| 25 STD | 15599 | — | 25 STD | 7788 | — |
| 50 STD | 14208 | — | 50 STD | 6950 | — |
| 100 STD | 11025 | — | 100 STD | 5739 | — |
| 250 STD | 8500 | — | 250 STD | 4529 | — |
| 500 STD | 6659 | — | 500 STD | 3747 | — |
| 1000 STD | 4187 | — | 1000 STD | 2678 | — |
| Female | 10782 | 89 | Female | 5233 | 149 |
| Male #1 | 11403 | 118 | Male #1 | 3639 | 253 |
| Male #2 | 11794 | 111 | Male #2 | 3881 | 457 |
| Male #3 | 10842 | 94 | Male #3 | 3393 | 565 |

Virtually no difference in hormone level was obtained between any of the patients using the assay without the surfactant. However, by incorporating a surfactant in the incubation for the same serum sample in an otherwise identical method, the actual steroid levels were obtained.

The above-exemplified procedure can be used for assay of any of various other serum and plasma haptens by replacing the above testosterone components with the respective hapten components represented for illustration as follows:

| Hapten (Tracer) Solution, Standards, and Controls | Hapten Antiserum |
|---|---|
| Estriol ($^{125}$I) | Rabbit anti-human estriol antiserum. |
| 17-B-Estradiol ($^{125}$I) | Rabbit anti-human 17-B-estradiol antiserum. |
| DHEA-Sulfate ($^{125}$I) | Rabbit anti-human DHEA-sulfate antiserum. |
| Progesterone ($^{125}$I) | Rabbit anti-human progesterone antiserum. |
| Cortisol ($^{125}$I) | Rabbit anti-human cortisol antiserum. |

The following are examples of the assay method using enzyme immunoassay.

Preparation of Testosterone Enzyme Conjugate

Testosterone-3-carboxymethyloxime, 36.1 mg. (100 μmole), is dissolved in 1 ml. of dimethylformamide containing 3 drops of triethylamine. The solution is cooled to $-15°$ C., and 13.1 microliters (100 μmole) of isobutylchloroformate is added. The solution is stirred for 1 hour at $-15°$ to $-5°$ C. during which time the solution turns light orange.

Malate dehydrogenase 0.5 cc. of 10 mg./ml. suspension in 2.8 M ammonium sulfate (5 mg. MDH, $6.8 \times 10^{-6}$ mole MDH, $44 \times 10^{-6}$ mole lysine residue), is centrifuged at 15,000 r.p.m. for 20 minutes. The pellet is dissolved in 1 ml. of water and the solution is dialyzed against water at 4° C. for 5 hours (3 changes). The solution is brought to pH 8.5 with dilute NH$_4$OH at 4° C. and 44 l. of the mixed anhydride solution (4.4 μmole mixed anhydride; corresponds to 1 hapten per lysine) is added to the stirred enzyme solution in three portions over 5 minutes. Ammonium hydroxide solution is added as needed to keep the pH at 8.5. Initially the solution is turbid but clears during 1 hour stirring at 4° C. The solution is exhaustively dialyzed against 0.05 M. Phosphate buffer, pH 7.5. Sediment, if any, is removed by centrifugation.

Assay

Because of the instability of diluted enzyme solutions, the stock solution (5 mg/ml; $3.4 \times 10^{-5}$ M) is diluted 1 to 500 just prior to each assay. The order of addition of reagents to the assay mixture is as follows:

(1) antibody solution
(2) dilute system
(3) polyoxyethylene 9 lauryl ether 1.0% w/v, total
(4) oxaloacetic acid 0.01 M in 0.01 M phosphate buffer
(5) NADH, 1.3 mM
(6) Serum, 50–100 microliters The reagents are mixed, incubated for one hour, and the absorbance at 340 nanometers is read in a spectrophotometer. The result is calculated by comparison with calibrator standards and controls. The final enzyme concentration is ca. $2.7 \times 10^{-9}$ M. The antibody concentration is not known. Sufficient antibody is used to achieve greater than 40% inhibition of the enzyme activity.

(1) Enzyme Alone—0.073 OD/min. (2) 50–100 microliters serum or plasma which contains testosterone—0.073 OD/min. (3) Enzyme+Antibody—0.42 OD/min.

Preparation of Estradiol Enzyme Conjugate

To 33.0 mg. ($10^{-4}$ mole) of 3-(0-carboxymethyl)estradiol dissolved in 1 ml. of anhydrous dimethylformamide is added 2 drops of triethylamine. The solution is cooled to $-15°$, and 13.1 μl. ($10^{-4}$ mole) of isobutylchloroformate is added. The solution is maintained at $-15°$ for 1 hour.

The above solution (44 μl.) is added to a solution of 5 mg. malic dehydrogenase in 0.004 M $Na_2HPO_4$, pH 9 which has been cooled to 4°. During the reaction the pH is maintained at 8.5 to 9.0 by adding ammonium hydroxide solution. The solution, turbid initially, clears after 2 hours. It is dialyzed exhaustively against 0.05 M sodium phosphate, pH 7.5; then clarified by centrifugation.

Assay

The stock enzyme solution is diluted 1 to 1000 with 1 M $Na_2HPO_4$ solution and assayed in the above manner entailing reading the endpoint oxidation of reduced nicotinamide adenine dinucleotide (NADH) in the presence of oxaloacetic acid at 340 nm., 30° C. Antiestradiol antibodies are prepared in rabbits and the γ-globulin ($4 \times 10^{-7}$ M binding sites) fraction is used in this assay.

While the invention is described in detail in the foregoing specification, it will be realized by those skilled in the art that considerable variation can be made in such detail without departing from the spirit and scope of the claims which follow.

We claim:

1. A storage-stable reagent kit for assay of a selected hapten in an aliquot of body fluid containing lipid, comprising a first container containing a tracer in liquid form including a non-lipid conjugate of said hapten, containers separate from said first container respectively containing first and second competitive binding proteins for immunospecific mutual binding with said hapten and conjugate, and surfactant in said liquid tracer for constituting in an incubation mixture with the aliquot in a quantity sufficient for solubilizing the mixture.

2. A reagent kit according to claim 1 comprising lipase in a quantity sufficient for converting to unbound form any of said hapten present in the incubation mixture in lipid-bound form.

3. A reagent kit according to claim 1 where the tracer is radioactive.

4. A reagent kit according to claim 1 where the selected hapten is testosterone.

5. A reagent kit according to claim 4 where the competitive binding proteins are rabbit anti-human testosterone antiserum and goat anti-rabbit antibody.

6. A reagent kit according to claim 4 where the conjugate is $^{125}$I-O-(2-iodohistaminylcarboxamidomethyl)-testosterone oxime.

7. A method for assay of a selected hapten in an aliquot of body fluid containing lipid employing a reagent kit according to claim 1, which comprises constituting the aliquot in a mixture comprising said surfactant and incubating the mixture, the quantity of surfactant being sufficient to solubilize the mixture.

8. A method according to claim 7 which comprises incubating the mixture with lipase in a quantity sufficient for converting to unbound form any of said hapten present in the mixture in lipid-bound form.

9. A method according to claim 7 where the hapten is testosterone.

10. A method according to claim 7 which comprises constituting the aliquot in an antibody binding site mixture comprising lipase, surfactant, a tracer which includes a non-lipid conjugate of said hapten, and a first antibody which is specific to said hapten, and incubating the mixture to solubilize the same, convert the bound hapten to unbound hapten and bind unbound hapten with the hapten-specific antibody.

11. A method according to claim 10 where the hapten is testosterone.

12. A method according to claim 11 where the conjugate is $^{125}$I-O-(2-iodohistaminylcarboxamidomethyl)testosterone oxime.

13. A method according to claim 11 where the antibody is rabbit anti-human testosterone antiserum.

14. A method according to claim 10 comprising incorporating the incubated mixture with a second antibody which is specific to said hapten-specific antibody.

15. A method according to claim 14 where the first antibody is rabbit anti-human hapten anti-serum.

16. A method according to claim 14 where the second antibody is goat anti-rabbit hapten antibody.

17. A method according to claim 14 where the tracer conjugate is radioactive, comprising isolating the resulting radioactive hapten-first antibody-second antibody product and reading the hapten content thereof radiometrically.

18. A method for assay of a selected hapten in an aliquot of body fluid containing hapten bound to carrier protein, employing a reagent kit according to claim 1, which comprises constituting the aliquot in a mixture comprising said surfactant and incubating the mixture, the quantity of surfactant being sufficient to dissociate the hapten from the carrier protein.

* * * * *

UNITED STATES PATENT AND TRADEMARK OFFICE
CERTIFICATE OF CORRECTION

PATENT NO. : 4,452,903
DATED : June 5, 1984
INVENTOR(S) : Jin P. Lee & Ching Sui A. Yi It is certified that error appears in the above-identified patent and that said Letters Patent are hereby corrected as shown below:

Column 1, line 55, after "These" insert --above-mentioned prior art--.

Column 8, line 25, delete "components" and insert "component".

Signed and Sealed this

Fourteenth Day of May 1985

[SEAL]

Attest:

DONALD J. QUIGG

Attesting Officer     Acting Commissioner of Patents and Trademarks